United States Patent [19]

Matsumoto et al.

[11] Patent Number: 5,712,388
[45] Date of Patent: Jan. 27, 1998

[54] METHOD OF PREPARING A DERIVATIVE OF OPTICALLY ACTIVE AZETIDIN-2-ONE

[75] Inventors: Takaji Matsumoto; Toshiyuki Murayama; Takashi Miura, all of Kanagawa, Japan

[73] Assignee: Takasago International Corporation, Tokyo, Japan

[21] Appl. No.: 648,516

[22] Filed: May 13, 1996

[30] Foreign Application Priority Data

May 11, 1995 [JP] Japan ................... 7-135614

[51] Int. Cl.$^6$ ............................... C07D 205/08
[52] U.S. Cl. ............................... 540/362
[58] Field of Search ............................... 540/362

[56] References Cited

U.S. PATENT DOCUMENTS

| | | | |
|---|---|---|---|
| 4,981,992 | 1/1991 | Sayo et al. | 560/23 |
| 5,204,461 | 4/1993 | Murayama et al. | 540/362 |
| 5,241,064 | 8/1993 | Murata et al. | 540/362 |
| 5,463,047 | 10/1995 | Schneider et al. | 540/362 |

Primary Examiner—Mukund J. Shah
Assistant Examiner—Deepak R. Rao
Attorney, Agent, or Firm—Sughrue, Mion, Zinn, Macpeak & Seas, PLLC

[57] ABSTRACT

To prepare the compound (1'R,3S)-3-(1'-tri-substituted silyloxyethyl)azetidin-2-one, (2S,3R)-2-aminomethyl-3-hydroxybutyric acid is reacted with an alcohol in the presence of at least one compound chosen from the group consisting of thionyl chloride, hydrogen chloride and p-toluene sulfonic acid, thereby obtaining a salt of the corresponding ester. The salt is reacted with a tri-substituted silane in the presence of a metallic catalyst, thereby protecting the hydroxy group of the ester and then reacted with a base, thereby obtaining an ester of (2S,3R)-2-aminomethyl-3-(tri-substituted silyloxy)butyric acid. Subsequently, the ester is transformed into lactam in the presence of a Grignard reagent or a metal amide, thereby obtaining (1'R,3S)-3-(1'-tri-substituted silyloxyethyl) azetidin-2-one. This compound provides a useful base for preparing β-lactam type antimicrobial agents such as carbapenem type agents.

8 Claims, No Drawings

METHOD OF PREPARING A DERIVATIVE OF OPTICALLY ACTIVE AZETIDIN-2-ONE

BACKGROUND OF THE INVENTION (1) Field of the Invention

The present invention relates to a method of preparing (1'R,3S)-3-(1'-tri-substituted silyloxyethyl)azetidin-2-one having the formula (I):

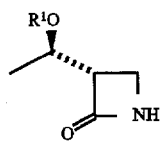

(I)

wherein $R^1$ is a tri-substituted silyl group.

This compound is a useful intermediate product for the synthesis of carbapenem-type antimicrobial agents represented by thienamycin.

β-lactam type antimicrobial agents, such as carbapenem-type agents, have currently been attracting the greatest interest as antimicrobial substances. These anti-microbial agents all have a (1'R,3S)-3-(1'-hydroxyethyl)azetidin-2-one unit as common base structure.

The present invention provides a method of manufacturing (1'R,3S)-3-(1'-t-butyldimethylsilyloxyethyl)azetidin-2-one, which is aptly configured for the synthesis of the above-mentioned β-lactam type agents and serves as a useful base for this synthesis.

(2) Description of the Prior Art

The synthesis of this starting material was previously reported by NOYORI et al. in J. Am. Chem. Soc., III, 9134 (1989); and Japanese published application (Kokai) Hei 2-134 349 by Takasago International Corporation. According to these documents, 2-amidomethyl acetoacetate is asymmetrically hydrogenated, hydrolyzed with acid, transformed into lactam and silylated, as shown in the following scheme:

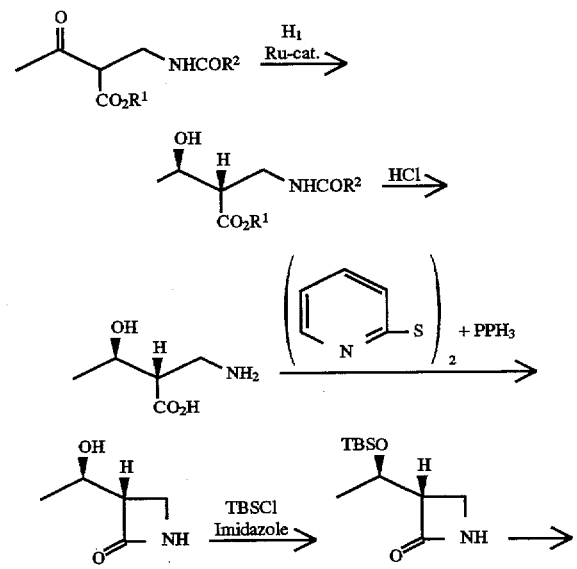

David A. EVANS et al. reported another method in Tetrahedron Letters 27, 4961 (1986). According to this method, an imide is first synthesized from an optically active oxazolidone and a crotonic acid chloride. As shown in the following scheme, this imide and acetaldehyde are firstly asymmetrically aldol-condensed in the presence of a boron reagent and led to the desired compound via a total of 7 steps:

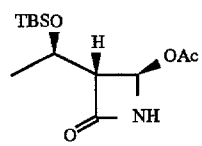

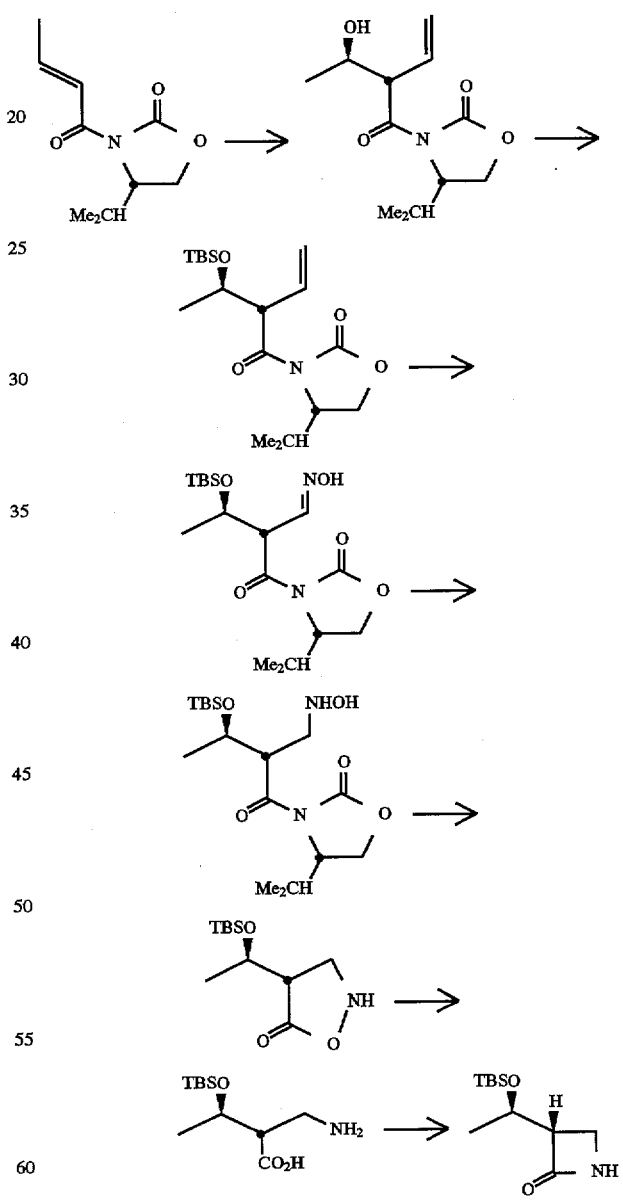

According to Japanese published application Hei 4-173 795 by Takasago International Corporation, 2-amidomethyl acetoacetate is asymmetrically hydrogenated and hydrolyzed to obtain (2S,3R)-2-aminomethyl-3-hydroxybutyric acid. This product is reacted with t-butyl dimethylchlorosilane (TBSCl) to obtain (2S,3R)-2-aminomethyl-3-(t-butyldimethylsilyloxy)butyric acid. This product is subsequently transformed into lactam by using 2,2'-dibenzothiazolyldisulfide and triphenylphosphine as shown in the following scheme:

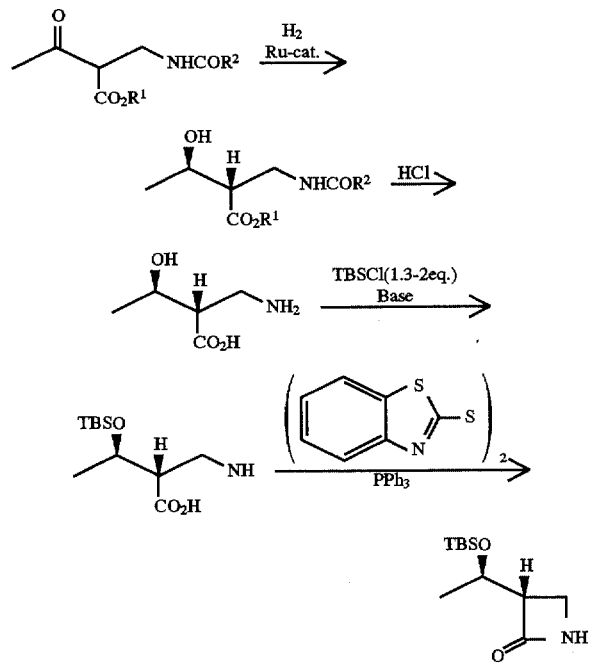

As a variant, Japanese published application Hei 4-173 776 by Takasago International Corporation discloses the use of a sulpheneamide derivative and triphenylphosphine for the transformation into lactam, as shown in the following scheme:

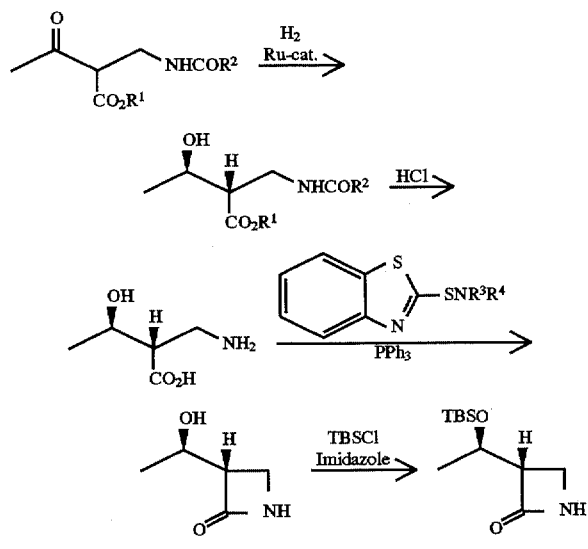

Further, according to the Japanese published application Hei 5-239 019 by Takasago International Corporation, 2-phthalimidomethyl acetoacetate is asymmetrically hydrogenated silylated and freed from 2-phthalimide protection by hydrazine to obtain (2S,3R)-2-aminomethyl-3-(t-butyldimethylsilyloxy) butyric acid ester. This ester is subsequently transformed into lactam by a Grignard reagent as shown in the following scheme:

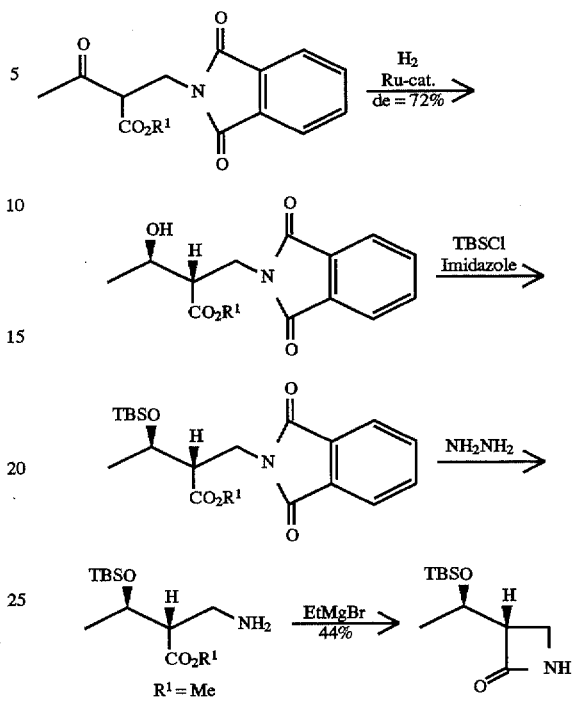

Furthermore, according to U.S. Pat. No. 4,927,507 (Japanese published application Sho 63-297 360) by Ciba Geigy Co. Ltd., 2-amidomethyl acetoacetate is transformed into a cyclic derivative of 5,6-dihydro-1,3,4H-oxazinyl-5-carboxylic acid ester. Subsequently, this derivative is asymetrically transformed into a favourable configuration, hydrolyzed, transformed into lactam and silylated, as shown in the following scheme:

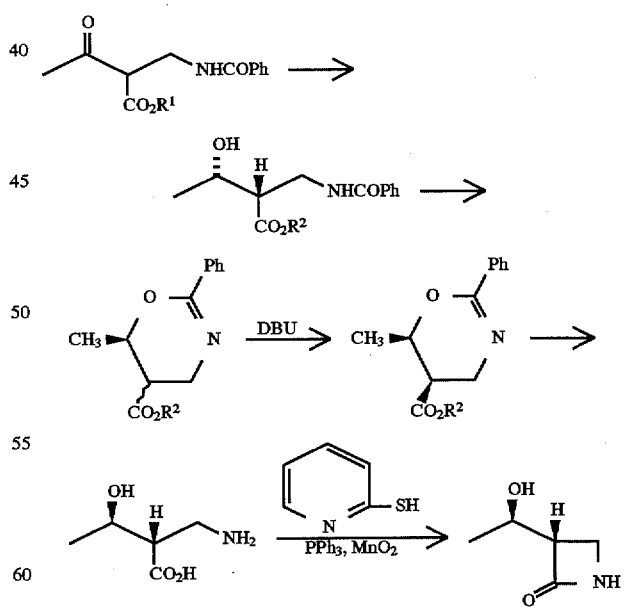

It should be noted that the method by NOYORI et al. (Japanese published application Hei. 2-134 349) uses a stereo-selective asymmetric hydrogenation to obtain amidoalcohol, which is then hydrolyzed into hydroxy amino acid and the latter is subsequently transformed into lactam.

This transformation requires relatively costly dipyridyldisulfide, which is a drawback for industrial utilization.

The method by EVANS et al. contains many steps and has the additional drawback of using expensive reagents.

With the method disclosed in U.S. Pat. NO. 4,927,507, diastereomers have to be separated from the derivative of 5,6-dihydro-1,3,4-H-oxazinyl-5-carboxylic acid ester. This separation and subsequent purification are very cumbersome and involve numerous steps. Moreover, triphenylphosphine-dipyridyldisulfide complex and triphenylphosphine-mercaptopyridine-manganese dioxide complex used for lactam-forming tend to increase industrial waste.

With the method disclosed in Japanese published application Hei 4-173 795, silylation requires a relatively costly reagent. Further, dibenzothiazolyldisulfide and triphenylphosphine used for lactam formation have the drawback of increasing waste.

With the method disclosed in Japanese published application Hei 5-239 019, the asymmetric hydrogenation has a low selectivity, whilst the yield of lactam, formed by a Grignard reagent, is relatively low.

SUMMARY OF THE INVENTION

Therefore an object of the present invention is to solve the above-mentioned problems and to provide a new and simpler reaction process for efficiently preparing (1'R,3S)-3-(1'-tri-substituted silyloxyethyl)azetidin-2-one of formula (I).

To this end, there is provided a method of preparing a derivative of optically active azetidin-2-one comprising the steps of:

a) reacting (2S,3R)-2-aminomethyl-3-hydroxybutyric acid having formula (II):

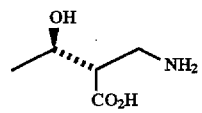

(II)

with an alcohol in the presence of at least one compound chosen from the group consisting of thionyl chloride, hydrogen chloride and p-toluene sulfonic acid, thereby obtaining a salt of (2S,3R)-2-aminomethyl-3-hydroxybutyric acid ester having formula (III)

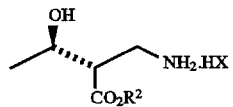

(III)

where $R^2$ is an alkyl group having 1 to 5 carbon atoms and X is selected from the group consisting of a chlorine atom and a p-toluene sulfonyloxy group;

b) reacting the salt (III) with a tri-substituted silane compound in the presence of a metallic catalyst, thereby obtaining a salt of (2S,3R)-2-aminomethyl-3-(tri-substituted silyloxy)butyric acid ester having formula (IV):

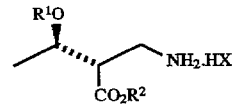

(IV)

where $R^1$ is a trisubstituted silyl group, and $R^2$ and X are as indicated in the preceding formula;

c) reacting the salt (IV) with a base, thereby obtaining an ester of (2S,3R)-2-aminomethyl-3-(tri-substituted silyloxy)butyric acid having formula (V):

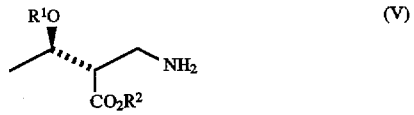

(V)

where $R^1$ and $R^2$ are as indicated in the preceding formula; and d) transforming the ester (V) into a lactam in the presence of a member selected from the group consisting of a Grignard reagent and a metal amid, thereby obtaining (1R,3S)-3-(1-tri-substituted silyoxyethyl)azetidin-2-one.

The tri-substituted silane used in step b) may be t-butyldimethylsilane, triethylsilane, triphenylsilane or phenyldimethylsilane. The 1'-tri-substituted silyloxyethyl group obtained in step d) is then respectively 1'-t-butyldimethylsilyloxyethyl, 1'-triethylsilyloxyethyl, 1'-triphenylsilyloxyethyl or 1'-phenyldimethylsilyloxyethyl.

Preferably, the alcohol used in step a) is methanol $R^2$ is then a methyl group.

The Grignard reagent used in step d) is preferably a t-alkyl Grignard reagent.

As to step d), the preferred embodiment involves addition of the ester (V) to the Grignard reagent or metal amide, compared to the other way around.

There is also provided a process of preparing a β-lactam type antimicrobial substance comprising the method as set forth in claim 1.

To render into practice the above-mentioned method, a salt of (2S,3R)-2-aminomethyl-3-hydroxybutyric acid ester of the formula (III) and a salt of (2S,3R)-2-aminomethyl)-3-(tri-substituted silyloxy)butyric acid ester of the formula (IV) were prepared as new intermediate products.

DETAILED DESCRIPTION OF THE PREFERRED EMBODIMENTS

The above and other objects, features and advantages of the invention will be made apparent from the following description of the preferred embodiments, given as a non-limiting example.

The starting material of the present invention is (2S,3R)-2-aminomethyl-3-hydroxybutyric acid of formula (II).

This material is easily obtained by a known method (such as that described in Japanese published application Hei 2-134 349). According to this method, a 3-oxobutanoic acid (3-oxobutyric acid) ester is asymmetrically hydrogenated using a complex of Ruthenium-optically active phosphine as catalyst, thereby obtaining 3-hydroxybutanoic acid. The latter is hydrolyzed in diluted hydrochloric acid solution or similar, neutralized with sodium hydroxide and concentrated to obtain the desired starting material.

(2S,3R)-2-aminomethyl-3-hydroxybutyric acid of formula (II) is transformed into a salt of (2S,3R)-2-aminomethyl-3-hydroxybutyric acid ester of formula (III) by a known method according to N. IZUMIYA et al. ("Peptide Synthesis; basis and experiments", Maruzen, p. 926, (1985) or BRENNER et al. (Helv. Chim. Acta, 36, 1109, 1953), the compound (II) is reacted, in an alcohol, with at least one compound chosen from the group consisting of thionyl chloride, hydrogen chloride and p-toluene sulfonic acid, to obtain the compound (III). The alcohol used is, for example, methanol, ethanol, propanol or butanol.

In compound (III), the amino group is protected by virtue of being in the form of ammonium salt, so that only the hydroxy group is free for silylation.

Compound (III) is then silylated by using a metallic catalyst and tri-substituted silane compound, to obtain a compound of formula (IV).

The metallic catalyst used is, for example, palladium-carbon, palladium chloride, palladium acetate, palladium-alumina, palladium-silica-alumina, etc.

The tri-substituted silane compound is preferably an aryl or alkyl substituted one, which is for example, triethylsilane, t-butyldimethyl silane triphenylsilane, phenyldimethylsilane, etc. The reaction solvent used is, for example, acetonitrile, propionitrile, N,N-dimethyl acetamide, N-methyl pyrrolidone, 1,3-dimethyl-2-imidazolidinone, methyl acetate, ethyl acetate, n-butyl acetate, methyl isobutyl ketone, toluene, etc.

Reaction conditions can be appropriately modified and are not confined to a specific limit. For example, the compound (III) and a metallic catalyst are suspended in a solvent; then a tri-substituted silane is added to the solvent, either dropwise or in one batch, and the mixture is reacted for about one to 24 hours, preferably one to 3 hours at a temperature of 30° to 100° C., preferably 60° to 90° C.

Tri-substituted silane is added in a molar proportion of 1.0 to 1.5, preferably 1.0 to 1.1, relative to the compound (III).

The metallic catalyst is added in a molar proportion of about 1/50 to 1/1000, preferably 1/50 to 1/200, with respect to the compound (III).

The compound (IV) thus obtained is treated with an alkali solution such as sodium hydrogen carbonate, sodium carbonate, sodium hydroxide or potassium hydroxide, to obtain an alkyl {(2R,3S)-2-aminomethyl-3-(tri-substituted silyloxy)} butyrate (V).

Subsequently, the compound (V) is transformed into lactam in the presence of a Grignard reagent or a metal amide, to obtain (1'R,3S)-3-(1'-tri-substituted silyloxyethyl) azetidin-2-one (1): this reaction is effected in an ether-type solvent such as diethylether, tetrahydrofuran, 1,3-dioxolane etc., in a hydrocarbon-type solvent such as hexane, heptane, toluene, etc., or in a mixture thereof.

The Grignard reagents used have the formula (VI)

$R^3MgY$ (VI)

where $R^3$ is an alkyl group having 1 to 6 carbon atoms, an aralkyl group or an aryl group and Y is a halogen atom.

Examples of the Grignard reagent used are an alkyl Grignard reagent such as ethyl magnesium chloride, ethyl magnesium bromide, isopropyl magnesium bromide, n-butyl magnesium chloride, n-butyl magnesium bromide, t-butyl magnesium chloride, t-butyl magnesium bromide, t-amyl magnesium chloride, t-amyl magnesium bromide, etc; an aralkyl Grignard reagent such as benzyl magnesium chloride etc; and an aryl Grignard reagent such as phenyl magnesium bromide etc.

The preferred reagent is a t-alkyl Grignard reagent such as t-butyl magnesium chloride, t-butyl magnesium bromide, t-amyl magnesium chloride, t-amyl magnesium bromide, etc.

The metal amide used is, for example, lithium diethyl amide, lithium diisopropyl amide, etc.

The amount of Grignard reagent or metal amide used is at least 2 moles, preferably 2 to 4 moles, relative to 1 mole of the alkyl butyrate (V).

Temperatures and duration of the reaction may be appropriately chosen and are not confined to a specific limit. Usually, the reaction is effected for 0.5 to 24 hours at −20° C. to +30° C., preferably −5° to +15° C.

In the reaction, a Grignard reagent or metal amide may be added to the solution of alkyl butyrate (V0 or vice versa. However, preferably the solution of alkyl butyrate (V) is added to the solution of a Grignard reagent or metal amide.

EXAMPLES

Apparatus and conditions used in the above embodiments are as follows:

melting temperature measuring apparatus: MP-500D, manufactured by Yanako Instituted for apparatus development;

Infrared (IR) absorption spectrum measuring apparatus: IR-810 type, manufactured by Nippon Bunko Industries Co.;

$^1$H NMR spectrum measuring apparatus: AM-400 type (400 MHz), manufactured by Bruker Corp.;

Internal Standard Substances: tetramethyl silane (in $CDCl_3$), 3-(trimethylsilyl)-1-propane sulfonic acid, sodium salt (in $D_2O$).

The final product of the embodiments contained no isomerized counterpart. This fact was confirmed by a gas chromatography operation having the following features:

Analyzing unit: HP-5890 manufactured by Hewlett Packard Co.;

Column: Neutrabond-1 (0.25 mm×30 m), manufactured by GL Sciences Co.;

Conditions: Helium carrier; injection at 200° C.; detection at 250° C.; initial temperature of 100° C.; final temperature of 250° C.; and heating rate of 5° C./min;

and/or by NMR measurement.

Preparation of the starting material Synthesis of (2S,3R)-2-aminomethyl-3-hydroxybutyric acid (II).

The above compound was synthesized according to the method disclosed in Japanese published application Hei 2-134 349.

An autoclave made of stainless steel was previously filled with nitrogen and used in the following reaction. 25.0 g (0.1 mole) of methyl 2-(N-benzoylamino)methyl-3-oxobutyrate, and 850 mg (1.0 mmole) of the complex of ruthenium-optically active phosphine, $Ru_2Cl_4((+)-BINAP)_2NEt_3$, were dissolved in 175 ml of methylene chloride. The solution was placed in the above autoclave and asymmetrically hydrogenated by stirring for 20 hours at 50° C., under 100 Kg/cm² of hydrogen pressure. After the hydrogenation, the solvent was distilled. The residue was applied to a chromatography column on silica gel and eluted with a mixture of ethyl acetate and hexane (1:1), to obtain 20.08 g (0.08 mole) of methyl (2S,3R)-2-(N-benzoylamino)methyl-3-hydroxy butyrate. Yield was 87%.

The above compound was transformed into (R)-(+)-α-methoxy-α-trifluoromethylphenylacetate. The optical purity of the obtained product was determined to be 98% by a high speed liquid chromatography under the following conditions:

Column: Develosil 100-3 (4.6 mm×250 mm), manufactured by Nomura Kagaku Co.

Measured wave length: 254 nm elution mixture: hexane:diethyl ether (9:1)

elution speed: 1 ml/min 20.08 g (0.08 mole) of methyl (2S,3R)-2-(N-benzoyl amino)methyl-3-hydroxybutyrate were dissolved in 60.8 g of 12N-hydrochloric acid solution, refluxed with application of heat for 6 hours and cooled to room temperature, so that a solid was precipitated. After the solid was filtered, the filtrate was washed twice with 100 ml of toluene. Then a water phase was concentrated to a residue in vacuo. To this was added 250 ml of acetonitrile and further, under an ice water cooling, 0.08 g (0.08 mole) of triethylamine. The total solution was stirred overnight at room temperature to yield precipitates. The precipitates were filtered, washed with 200 ml of acetonitrile and dried in vacuo, thereby obtaining 8.51 g (0.06 mole) of (2S,3R)-2-aminomethyl-3-hydroxybutyric acid. Yield was 80%. This compound corresponded to that described in the Japanese published application Hei 2-134 349 according to an $^1$H-NMR spectrum analysis.

Example 1

Synthesis of methyl (2S,3R)-2-aminomethyl-3-hydroxybutyrate hydrochloride, of the formula (III) where $R^2$ is a methyl group and X is a chlorine atom.

In a nitrogen atmosphere, 18.49 g (0.139 mole) of (2S,3R)-2-aminomethyl 3 hydroxybutyric acid were suspended in 70 ml of methanol, stirred at −5° C. and 17.35 g (0.146 mole) of thionyl chloride were added dropwise, during a time period of 10 minutes. The suspension was then stirred overnight at 15° to 20° C. in a nitrogen atmosphere. At this stage, a high speed liquid chromatography confirmed the disappearance of the starting material.

The operational conditions of the chromatography were as follows:
column: Inertsil ODS-2 (4.6 mm×250 mm); manufactured by GL Sciences Co. Ltd.
measured wave length; 210 nm
elution mixture: acetonitrile: 0.02M-potassium dihydrogen phosphate (4:96)
elution speed: 0.5 ml/min Subsequently, methanol was removed in vacuo from the reaction solution. The resultant residue was added to 170 ml of acetonitrile and dissolved completely thereinto at 60° C. The solution was then cooled to room temperature, a further 15 ml of acetonitrile was added, the solution cooled to −5° C. and stirred for 30 minutes at this temperature, to obtain crystals. The crystals were filtered and dried to obtain 23.41 g of methyl (2S,3R)-2-aminomethyl-3-hydroxybutyrate hydrochloride. Yield was 91.8%.

The obtained product showed the following spectral features:
IR (in KBr pellet): 1740 cm$^{-1}$
NMR (in D$_2$O): 1.27 (d, J=6.5 Hz, 3H); 2.9 (m, 1H); 3.33 (dd, J=4.3 Hz, 13.4 Hz, 1H); 3.39 (dd, J=8.4 Hz, 13.4 Hz, 1H); 3.80 (s, 3H); 4.43 (dq, J=5.0 Hz, 6.5 Hz, 1H).

Example 2

Synthesis of methyl (2S,3R)-2-aminomethyl-3-(t-butyl dimethylsilyloxy)butyrate, of the formula (V) where $R^1$ is a t-butyl dimethylsilyl group and $R^2$ is a methyl group.

5.51 g (30.0 mmoles) of methyl (2S,3R)-2-aminomethyl-3-hydroxybutyrate hydrochloride and 27.5 mg (0.5 wt. %) of 5% palladium silicoalumina were suspended in 30 of N-methyl pyrrolidone, heated to 80° C. and stirred in a nitrogen stream until the hydrochloride was dissolved. Subsequently, 3.84 g (33.0 mmoles) of t-butyldimethylsilane were added dropwise during a time period of 2 hours in a nitrogen stream. After the addition, the mixture was further stirred for 17 hours at 80° C. in a nitrogen stream, cooled to room temperature and concentrated in vacuo. The concentrate was supplemented with 50 ml of toluene and filtered with celite auxiliary filtering agent, to remove the catalyst. The filtrate was supplemented with 50 ml of 10% sodium carbonate solution and stirred for 30 minutes. After fractionating, the obtained toluene phase was washed with 30 ml of water and condensed in vacuo. The resulting crude product was distilled at 73° C. at a pressure of 40 Pa (0.3 mm Hg), to obtain 6.89 g (26.4 mmoles) of an oily product consisting of methyl (2S,3R)-2-aminomethyl-3-(t-butyldimethylsilyloxy)butyrate. Yield was 88.0%.

The obtained product showed the following spectral features:
IR (neat sample): 1740 cm$^{-1}$
NMR (in CDCl$_3$): 0.04 (S,3H); 0.06 (s, 3H); 0.87 (s, 9H); 1.18 (d, J=6.2 Hz, 3H); 2.45 (ddd, J=4.5 Hz, 6.7 Hz, 8.3 Hz, 1H); 2.98 (dd, J=4.5 Hz, 13.0 Hz, 1H); 3.04 (dd, J=8.3 Hz, 13.0 Hz, 1H); 3.70 (m, 1H); 4.12 (m, 1H).

Example 3

Synthesis of methyl (2S,3R)-2-aminomethyl-3-triethyl silyloxybutyrate, of the formula (V) where $R^1$ is a triethylsilyl group and $R^2$ is a methyl group.

3.67 g (20.0 mmoles) of methyl(2S,3R)-2-aminomethyl-3-hydroxybutyrate hydrochloride and 10.7 mg (0.06 mmole) or palladium chloride were suspended in 30 ml of acetonitrile, heated to 80° C. and stirred in a nitrogen stream until the hydrochloride was dissolved 2.33 g (21.0 mmoles) of triethylsilane were then added dropwise during a time period of 20 minutes in a nitrogen stream. After the addition, the solution was further stirred for 3 hours in a nitrogen stream, cooled to room temperature and filtered with celite. After the filtrate was concentrated in vacuo, the residue was added to 50 ml of toluene and 40 ml of saturated sodium hydrogen carbonate solution, and stirred for 20 minutes. After fractionating, the toluene phase was washed with 30 ml of water and dried with anhydrous magnesium sulfate. After filtration, the filtrate was condensed in vacuo to obtain a crude product. The latter was applied to a chromatography column on a silica gel and eluted with a mixture of ethyl acetate and hexane (1:1), to obtain 4.25 g (16.3 mmoles) of an oily product consisting of methyl (2S,3R)-2-aminomethyl-3-triethylsilyloxybutyrate. Yield was 81.5%.

The obtained product showed the following spectral features:
IR (neat sample): 1740 cm$^{-1}$
NMR (in CDCl$_3$): 0.59 (q, J=7.9 Hz, 6H); 0.95 (t, J=7.9 Hz, 9H); 1.18 (d, J=6.2 Hz; 3H); 2.45 (m, 1H); 3.01 (m, 2H), 3.71 (s, 3H); 4.11 (dq, J=6.2 Hz, 7.2 Hz, 1H).

Example 4

Synthesis of methyl (2S,3R)-2-aminomethyl-3-triphenyl silyloxybutyrate, of the formula (V) where $R^1$ is a triphenyl silyl group and $R^2$ is a methyl group.

1.83 g (10.0 mmoles) of methyl (2S,3R)-2-aminomethyl-3-hydroxybutyrate hydrochloride, 5.3 mg (0.03 mmole) of palladium chloride and 2.76 g (10.6 mmoles) of triphenyl silane were suspended in 15 ml of acetonitrile and heated to 80° C. in a nitrogen atmosphere, the reaction solution was filtered with celite and the filtrate was concentrated in vacuo. residue obtained was supplemented with 30 ml of toluene and 30 ml of saturated sodium hydrogen carbonate solution and stirred for 20 minutes. After fractionating, the toluene phase was washed with 20 ml of water and dried with anhydrous magnesium sulfate. After filtration, the filtrate was concentrated in vacuo to obtain a crude product. The latter was applied to chromatography column on a silica gel and eluted with a mixture of ethyl acetate and hexane (1:1), to obtain 3.52 g (8.68 mmoles) of an oily product consisting of methyl(2S,3R)-2-aminomethyl-3-triphenylsilyloxybutyrate. Yield was 86.8%.

The obtained product showed the following spectral features:
IR (neat sample): 1735 cm$^{-1}$ NMR (in CDCl$_3$): 1.18 (d, J=6.2 Hz, 3H), 2.55 (ddd, J=4.0 Hz, 6.2 Hz, 8.6 Hz, 1H); 2.97 (dd, J=4.0 Hz, 13.1 Hz, 1H); 3.09 (dd, J=8.6 Hz, 13.1 Hz, 1H); 3.56 (s, 3H; 4.31 (dq, J=6.2 Hz, 6.2 Hz, 1H); 7.37–7.62 (m, 15H).

Example 5

Synthesis of (1'R,3S)-3-(1'-t-butyldimethylsilyloxyethyl) azetidin-2-one, of the formula I where R$^1$ is a t-butyldimethylsilyl group.

35 ml of 2M-tetrahydrofuran solution of t-butyl magnesium chloride and 25 ml of heptane were mixed, cooled to 0° C. while being stirred in a nitrogen atmosphere. 26 ml of heptane containing 7.31 g (28.0 mmoles) of methyl(2S,3R) -2-aminomethyl-3-(t-butyldimethylsilyloxy)butyrate were added, dropwise, thereto during a time period of 30 minutes in a nitrogen atmosphere. After the addition and 30 minutes of stirring in a nitrogen atmosphere, 100 ml of 1N-hydrochloric acid and 20 ml of heptane were added and further stirred. After fractionating, the organic phase was washed successively with 30 ml of saturated sodium hydrogen carbonate solution and with 30 ml of water. The organic phase was dried with anhydrous magnesium sulfate, filtered and concentrated, to obtain 6.02 g (26.2) mmoles) of (1'R, 3S)-3-(1'-t-butyldimethylsilyloxyethyl)azetidin-2-one. Yield was 93.6%.

The product obtained showed the following physical and spectral features:
melting temperature: 6.5°–68.0° C.
IR (in KBr pellet): 1750 cm$^{-1}$
NMR (in CDCl$_3$): 0.08 (s, 6H); 0.88 (s, 9H); 1.20 (d, J=6.2 Hz, 3H); 3.22 (m, 1H); 3.29 (dd, J=5.1 Hz, 5.3 Hz, 1H); 3.35 (m, 1H), 4.22 (m, 1H); 5.67 (broad s, 1H).

Example 6

Synthesis of (1'R, 3S)-3-(1'-t-butyldimethylsilyloxyethyl) azetidin-2-one, of the formula I where R$^1$ is a t-butyldimethylsilyl group.

To 10 ml of tetrahydrofuran containing 0.88 g (12 mmoles) of diethylamine were added, dropwise, 6.25 ml of 1.6M-hexane solution of n-butyl lithium (10 mmoles) at 0° C. in a nitrogen atmosphere, so as to prepare a lithium diethyl amide solution. This solution was added dropwise to 5 ml of ice-cooled tetrahydrofuran containing 1.31 g (5.0 mmoles) of methyl (2S,3R)-2-aminomethyl-3-(t-butyldimethylsilyloxy)butyrate in a nitrogen atmosphere, during a time period of 30 minutes. After the addition, the solution was stirred for 10 minutes in a nitrogen atmosphere and 30 ml of water was added. The reaction solution was extracted with 30 ml of toluene. The organic phase was then washed with 30 ml of water and concentrated in vacuo. The thus obtained crude product was applied to a chromatography column on silica gel and eluted with a mixture of ethyl acetate and hexane (1:1), to obtain 0.92 g (4.0 mmoles) of (1'R,3S)-3-(1'-t-butyldimethylsilyloxyethyl)azetidin-2-one. Yield was 80%.

Example 7

Synthesis of (1'R,3S)-3-(1'-triethylsilyloxyethyl)azetidin-2-one, of the formula (I) where R$^1$ is a triethylsilyl group.

To 6 ml of 1M-tetrahydrofuran solution of t-butyl magnesium chloride were added dropwise while being stirred at 0° C., 3 ml of heptane containing 523.1 mg (2.00 mmoles) of methyl (2S,3R)-2-aminomethyl-3-triethylsilyloxybutyrate, during a time period of 15 minutes in a nitrogen stream. After the addition, the solution was stirred for further reaction for 30 minutes at 0° C. in a nitrogen stream. Then, the solution was supplemented with 7 ml of 1N-hydrochloric acid and extracted with 20 ml of heptane. The heptane phase was washed with 10 ml of saturated sodium chloride solution, dried with anhydrous magnesium sulfate and filtered. The filtrate was concentrated in vacuo, yielding a crude product. The latter was applied to a chromatography column on silica gel and eluted with a mixture of ethyl acetate and hexane (1:1), to obtain 406.1 mg (77 mmoles) of an oily product consisting of (1'R,3S)-3-(1'-triethylsilyloxyethyl)azetidin-2-one. Yield was 88.5%.

The obtained product showed the following spectral features:
IR (neat sample): 1760 cm$^{-1}$
NMR (in CDCl$_3$): 0.60 (q, J=7.9 Hz, 6H); 0.96 (t, J=7.9 Hz, 9H); 1.23 (d, J=6.2 Hz, 3H); 3.22 (m, 1H); 3.22 (m, 2H); 4.20 (dq, J=5.4 Hz, 6.2 Hz, 1H); 5.66 (broad s, 1H).

Example 8

Synthesis of (1'R,3S)-3-(1'-triphenylsilyloxyethyl)azetidin-2-one, of the formula (I) where R$^1$ is a triphenylsilyl group.

To 6 ml of 1M-tetrahydrofuran solution of t-butyl magnesium chloride was added dropwise, while being stirred at 0° C., a mixture of heptane (3 ml) and tetrahydrofuran (1 ml) containing 810.1 mg (2.00 mmoles) of methyl (2S,3R)-2-aminomethyl-3-triphenyl silyloxybutyrate, during a time period of 20 minutes in a nitrogen stream. After the addition, the solution was stirred for further reaction for 30 minutes at 0° C. in a nitrogen stream. The reaction solution was supplemented with 7 ml of 1N-hydrochloric acid and the mixture was extracted with 20 ml of heptane. The heptane phase was washed with 10 ml of saturated sodium chloride solution, dried with anhydrous magnesium sulfate and filtered. The filtrate was concentrated in vacuo to obtain a crude product. The latter was applied to a chromatography column on silica gel and eluted with a mixture of ethyl acetate and hexane (1:1), to obtain 605.5 mg (1.62 mmoles) of (1'R,3S)-3-(1'-triphenyl silyloxyethyl)azetidin-2-one. Yield was 81.0%.

The obtained product showed the following physical and spectral features:
melting temperature: 129°–130° C.
IR (neat sample): 1755 cm$^{-1}$
NMR (in CDCl$_3$): 1.26 (d, J=6.2 Hz, 3H); 3.23 (m, 1H), 3.34 (m, 2H); 4.31 (m, 1H); 5.61 (broad s, 1H); 7.25–7.65 (m, 15H).

Example 9

Synthesis of n-butyl (2S,3R)-2-aminomethyl-3-(t-butyl dimethylsilyloxy)butyrate, of the formula (IV) where R$^1$ is a t-butyl dimethylsilyl group and R$^2$ is a n-butyl group.

In a nitrogen atmosphere, 33.1 g (1.00 mole) of (2S,3R) -2-aminomethyl-3-hydroxybutyric acid were suspended in 500 ml of butanol, stirred at room temperature, 122.5 g (1.03 moles) of thionyl chloride were added dropwise during a time period of 30 minutes, and the resultant composition was stirred overnight at 35° C. After a high speed liquid chromatography confirmed the disappearance of the starting material, the butanol was eliminated in vacuo from the reaction solution. 100 ml of xylene were added to the residue and removed in vacuo with a trace of butanol, to obtain 229.5 g of oily and viscous crude product of n-butyl (2s, 3R)-2-aminomethyl-3-hydroxybutyrate hydrochloride. Yield was 102%.

6.60 g (29.2 mmoles) of the above hydrochloride salts, 63.0 mg (1 wt. %) of 5% palladium carbon and 30 ml of N-methyl pyrrolidone were heated to 80° C. and stirred in a nitrogen atmosphere until the salts were dissolved. To the solution, 4.46 g (38.4 mmoles) of t-butyldimethylsilane were added, dropwise, during a time period of 2.5 hours in a nitrogen atmosphere. The solution was stirred for a further 5 hours at 80° C. in a nitrogen atmosphere and cooled to room temperature. The reaction solution was condensed in vacuo, supplemented with 50 ml of toluene, further stirred and filtered with celite to remove the catalyst. The filtrate was supplemented with 50 ml of 10%—sodium carbonate solution and stirred for 30 minutes. After fractionation, the toluene phase was washed with 30 ml of water and concentrated in vacuo, to obtain a crude product. The latter was distilled at 113° C. at a pressure of 80 Pa (0.6 mm Hg), to obtain 7.71 g (25.4 mmoles) of an oily product consisting of n-butyl(2S,3R)-2-aminomethyl-3-(t-butyldimethylsilyloxy) butyrate. Yield was 87.0%.

The product showed the following spectral features:

IR (neat sample): 1730 cm$^{-1}$

NMR (in CDCl$_3$): 0.05 (s, 3H); 0.06 (s, 3H); 0.87 (s, 9H); 0.94 (t, J=7.4 Hz, 3H); 1.18 (d, J=6.1 Hz, 3H); 1.4 (m, 4H); 1.6 (m, 2H); 2.43 (ddd, J=4.7 Hz, 7.0 Hz, 8.1 Hz, 1H); 2.97 (dd, J=4.6 Hz, 13.0 Hz, 1H); 3.02 (dd, J≦8.1 Hz, 13.0 Hz, 1H); 4.1 (m, 3H).

Example 10

Synthesis of (1'R,3S)-3-(1'-t-butyldimethyl silyloxyethyl) azetidin-2-one, of the formula (I) where R$^1$ is a t-butyl dimethylsilyl group.

4.5 ml of 2M-tetrahydrofuran solution of t-butyl magnesium chloride (9.0 mmoles) and 3 ml of heptane were mixed at 0° C. while being stirred in a nitrogen steam. 3 ml of heptane containing 909 mg (3.0 mmoles) of n-butyl (2S,3R)-2-aminomethyl-3-(t-butyldimethylsilyloxy)butyrate were added, dropwise, to this mixture, during a time period of 15 minutes in a nitrogen stream. After the addition, the mixture solution was further stirred for 15 minutes in a nitrogen stream, supplemented with 50 ml of 1N-hydrochloric acid and 30 ml of heptane, and stirred for 20 minutes. After fractionation, the organic phase was successively washed with 30 ml of saturated sodium hydrogen carbonate solution and with 30 ml of water, dried with anhydrous magnesium sulfate, and filtered. The filtrate was concentrated in vacuo to obtain a crude product. The latter was applied to a chromatography column on silica gel and eluted with a mixture of ethyl acetate and hexane (1:1), to obtain 496 mg (2.16 mmoles) of (1'R,3S)-3-(1'-t-butyldimethyl silyloxyethyl)azetidin-2-one. Yield was 72%.

Example 11

Synthesis of (1'R,3S)-3-(1'-t-butyldimethylsilyloxyethyl) azetidin-2-one, of the formula (I) where R$^1$ is a t-butyldimethylsilyl group.

7.31 g (28.0 mmoles) of methyl (2S,3R)-2-aminomethyl-3-(t-butyldimethylsilyloxy)butyrate were dissolved in 26 ml of heptane in a nitrogen stream. The solution was supplemented, dropwise, with a mixture of 35 ml of 2M-tetrahydrofuran solution of t-butyl magnesium chloride and of 25 ml of heptane, at 0° C. while being stirred, during a time period of 30 minutes in a nitrogen stream. After the addition, the solution was stirred for 30 minutes in a nitrogen stream, 100 ml of 1N-hydrochloric acid and 20 ml of heptane were added, and the solution was further stirred. After fractionation, the organic phase was washed successively with 30 ml of saturated sodium hydrogen carbonate solution and with 30 ml of water, dried with anhydrous magnesium sulfate and filtered. The filtrate was concentrated in vacuo, to obtain a crude product. The latter was applied to a chromatography column on silica gel and eluted with a mixture of ethyl acetate and hexane (1:1), to obtain 3.33 g (14.5 mmoles) of (1'R,3S)-3-(1'-t-butyldimethylsilyloxyethyl)azetidin-2-one. Yield was 51.8%.

The product showed the same melting temperature and the same IR and NMR behaviour as the product obtained in Example 5.

Example 12

Synthesis of n-butyl (2S,3R)-2-aminomethyl-3-(t-butyl dimethylsilyloxy)butyrate, of the formula (V) where R$^1$ is a t-butyl dimethylsilyl group and R$^2$ is a n-butyl group.

10.1 g (50.0 mmoles) of (2S,3R)-2-aminomethyl-3-hydroxybutyric acid, 30.0 g (405.4 mmoles) of butanol and 9.99 g (52.5 mmoles) of p-toluene sulfonic acid (one hydrate) were refluxed overnight together with 30 ml of toluene, while being heated in a Dean-Stark apparatus. Formed water was distilled away and the resultant solution was concentrated in vacuo to obtain a viscous residue. The residue was dissolved in 20 ml of ether and 10 ml of hexane was added, to yield an oily precipitate. The precipitate was recovered by decantation, dissolved in 20 ml of ether and again precipitated by adding 10 ml of hexane. The oily precipitate, recovered by decantation, was put in vacuo to distill away any remaining solvent, thereby obtaining 16.72 g (46.3 mmoles) of crude product of n-butyl (2S,3R)-2-aminomethyl-3-hydroxybutyrate p-toluene sulfonic acid salt. Yield was 92.6%.

The product showed the following spectral features:

IR (neat sample): 1730 cm$^{-1}$

NMR (in D2O): 0.90 (t, J=7.4 Hz, 3H); 1.26 (d, J=6.5 Hz, 3H); 1.37 (m, 2H), 1.65 (m, 2H); 2.38 (s, 2H); 2.84 (m, 2H);p 3.34 (m, 2H); 4.20 (m, 2H); 4.28 (m, 1H); 735 (d, J=8.0 Hz, 2H); 7.68 (d, J=8.0 Hz, 2H).

3.61 g (10.0 mmoles) of the above crude product were dissolved in 15 ml of toluene, 0.04 g of 5% palladium carbon was added and the resultant composition was heated to 80° C. in a nitrogen stream. To this solution, 1.39 g (12.0 mmoles) of t-butyldimethylsilane were added, dropwise, during a time period of one hour in a nitrogen stream. After the addition, the solution was stirred overnight at the same temperature in a nitrogen stream. The reaction solution was cooled to room temperature and filtered with celite. The filtrate was washed with 20 ml of saturated sodium hydrogen carbonate solution, then with 50 ml of water and dried with anhydrous magnesium sulfate. The latter was then filtered off and the filtrate was concentrated in vacuo to obtain a residue.

The residue was applied to a chromatography column on silica gel and eluted with a mixture of chloroform and methanol (95:5), to obtain 2.41 g (7.95 mmoles) of n-butyl (2S,3R)-2-aminomethyl-3-(t-butyldimethylsilyloxy) butyrate in oily state. Yield was 79.5%.

The product showed the same IR and NMR behaviour as the one obtained in Example 9.

What is claimed is:

1. A method of preparing a derivative of optically active azetidin-2-one comprising the steps of:

a) reacting (2S,3R)-2-aminomethyl-3-hydroxybutyric acid having formula (II):

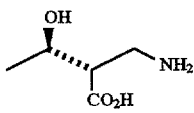

with an alcohol having 1 to 5 carbon atoms in the presence of at least one compound selected from the group consisting of thionyl chloride, hydrogen chloride and p-toluene sulfonic acid thereby obtaining a salt of (2S,3R)-2-aminomethyl-3-hydroxybutyric acid ester having formula (III):

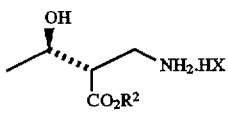

where $R^2$ is an alkyl group having 1 to 5 carbon atoms and X is selected from the group consisting of a chlorine atom and a p-toluene sulfonyloxy group;

b) reacting said salt (III) with a tri-alkyl or aryl substituted silane compound in the presence of a metallic catalyst selected from the group consisting of palladium, palladium-carbon, palladium chloride, palladium acetate, palladium-alumina and palladium-silica-alumina, thereby obtaining a salt of (2S,3R)-2-aminomethyl-3-(tri-substituted silyloxy)butyric acid ester having formula (IV):

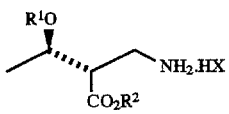

where $R^1$ is a tri-alkyl or aryl substituted silyl group, and $R^2$ and X are as indicated in the preceding formula;

c) reacting said salt (IV) with a base selected from the group consisting of an alkali metal hydroxide or a basic alkyl metal salt thereby obtaining an ester of (2S,3R)-2-aminomethyl-3-(tri-substituted silyloxy)butyric acid having formula (V):

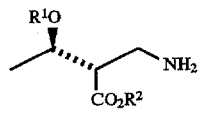

where $R^1$ and $R^2$ are as indicated in the preceding formula; and d) transforming the said ester (V) into a lactam in the presence of a member selected from the group consisting of a Grignard reagent selected from the group consisting of alkyl, aralkyl or aryl magnesium halides and a lithium metal amide, thereby obtaining (1R,3S)-3-(tri-substituted silyoxyethyl)azetidin-2-one having formula (I):

where $R^1$ is as indicated in the preceding formula.

2. A method according to claim 1, wherein the tri-substituted silane used in step b) is t-butyldimethylsilane and the 1'-tri-substituted silyloxyethyl group obtained in step d) is 1'-t-butyldimethylsilyloxyethyl.

3. A method according to claim 1, wherein the tri-substituted silane used in step b) is triethylsilane and the 1'-tri-substituted silyloxyethyl group obtained in step d) is 1'-triethylsilyloxyethyl.

4. A method according to claim 1, wherein the tri-substituted silane used in step b) is triphenylsilane and the 1'-tri-substituted silyloxyethyl group obtained in step d) is 1'-triphenylsilyloxyethyl.

5. A method according to claim 1, wherein the tri-substituted silane used in step b) is phenyldimethylsilane and the 1'-tri-substituted silyloxyethyl group obtained in step d) is 1'-phenyldimethylsilyloxyethyl.

6. A method according to claim 1, wherein the alcohol used in step a) is methanol and $R^2$ is a methyl group.

7. A method according to claim 1, wherein the Grignard reagent used in step d) is a t-alkyl Grignard reagent.

8. A method according to claim 1, wherein, in step d), the ester (V) is added to the member selected from the group consisting of said Grignard reagent and a said lithium metal amide.

* * * * *